(12) United States Patent
Paul et al.

(10) Patent No.: US 8,366,761 B2
(45) Date of Patent: Feb. 5, 2013

(54) DELIVERY SYSTEM WITH MEDICAL DEVICE RELEASE BY EVERTABLE SLEEVE

(75) Inventors: Ram H. Paul, Bloomington, IN (US); Brian C. Case, Lake Villa, IL (US); Brian P. Feng, Bloomington, IN (US); Frances Kristen Bailey, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/562,674

(22) Filed: Jul. 31, 2012

(65) Prior Publication Data

US 2012/0296412 A1   Nov. 22, 2012

Related U.S. Application Data

(63) Continuation of application No. 12/833,604, filed on Jul. 9, 2010.

(60) Provisional application No. 61/224,360, filed on Jul. 9, 2009.

(51) Int. Cl.
*A61F 2/06* (2006.01)
(52) U.S. Cl. ...................................... 623/1.11; 623/1.12
(58) Field of Classification Search ................. 623/1.11, 623/1.12, 1.13
See application file for complete search history.

(56) References Cited

U.S. PATENT DOCUMENTS

| | | | |
|---|---|---|---|
| 4,946,440 | A | 8/1990 | Hall |
| 5,779,670 | A | 7/1998 | Bidwell et al. |
| 2001/0044595 | A1 | 11/2001 | Reydel et al. |
| 2005/0240254 | A1 | 10/2005 | Austin |
| 2006/0030923 | A1 | 2/2006 | Gunderson |
| 2006/0041302 | A1 | 2/2006 | Malewicz |
| 2009/0018637 | A1 | 1/2009 | Paul, Jr. et al. |
| 2010/0168785 | A1 | 7/2010 | Parker |

OTHER PUBLICATIONS

N. M. Wilson, D. L. Rutt and N. L. Browse, Repair and replacement of deep vein valves in the treatment of venous insufficiency, Br. J. Surg. 1991, vol. 78, April, p. 388-394.

*Primary Examiner* — David Isabella
*Assistant Examiner* — Randy Shay
(74) *Attorney, Agent, or Firm* — Buchanan Nipper

(57) ABSTRACT

A medical device delivery system has a tubular member defining a passageway and an inner member slideably disposed within the passageway. An expandable intraluminal medical device is disposed on a chamber of the inner member, and an evertable sleeve is attached to the inner member proximal to the chamber and to an inner surface of the tubular member. Relative movement between the tubular and outer members moves the evertable sleeve from a first position substantially overlying the expandable intraluminal medical device to a second position substantially proximal to the chamber.

20 Claims, 5 Drawing Sheets

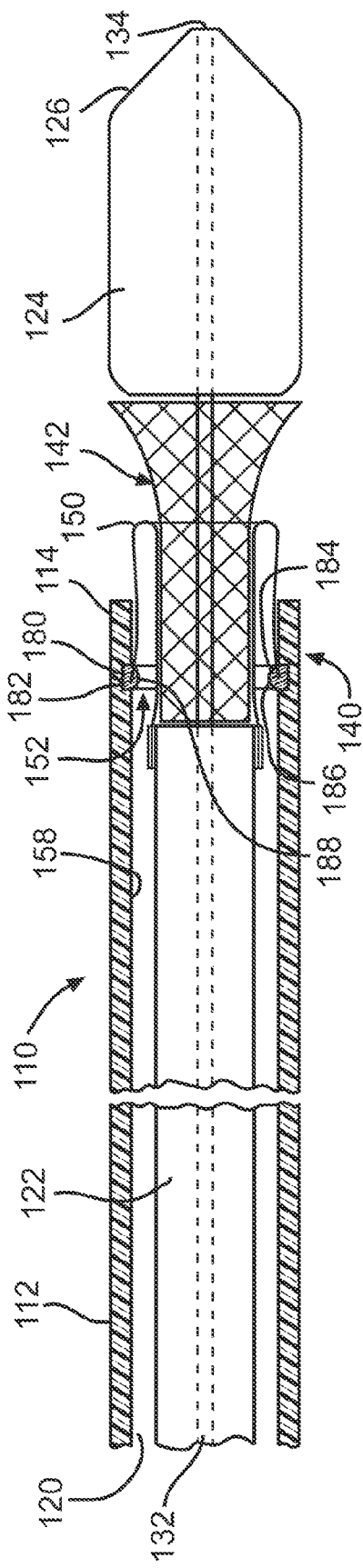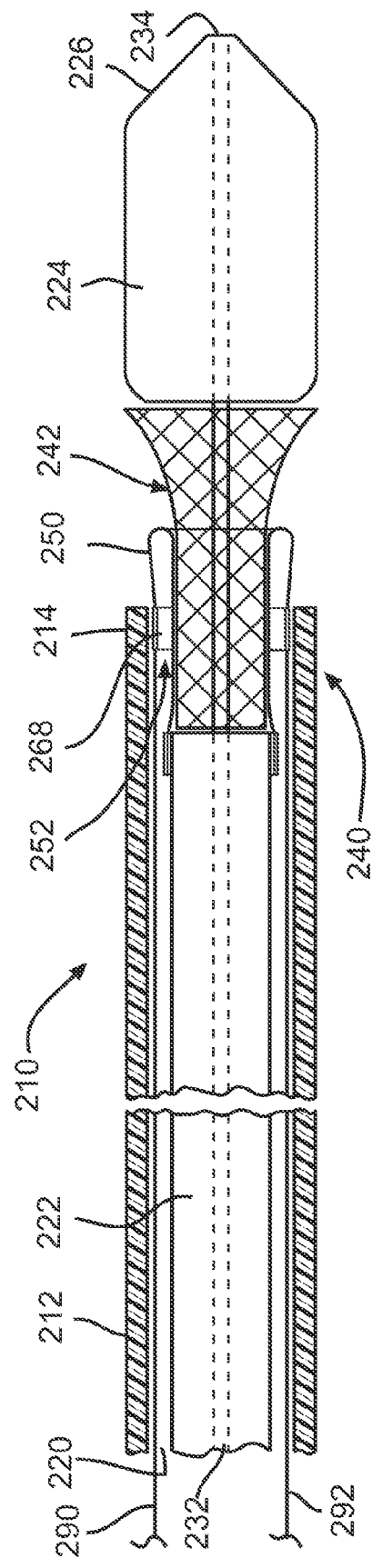

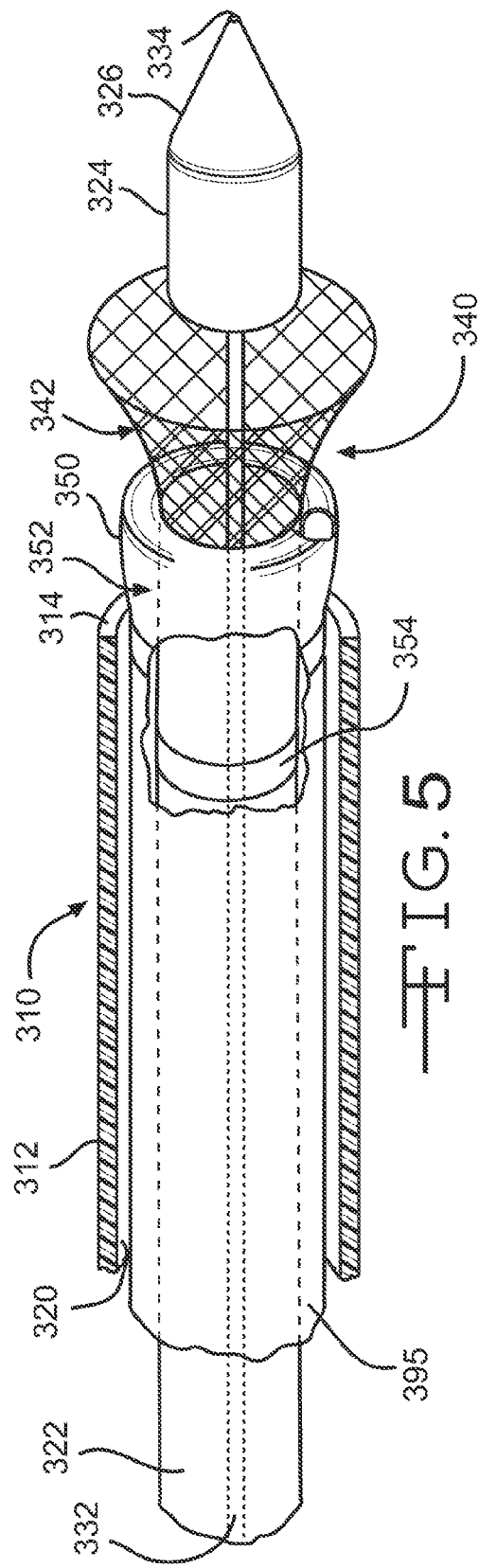
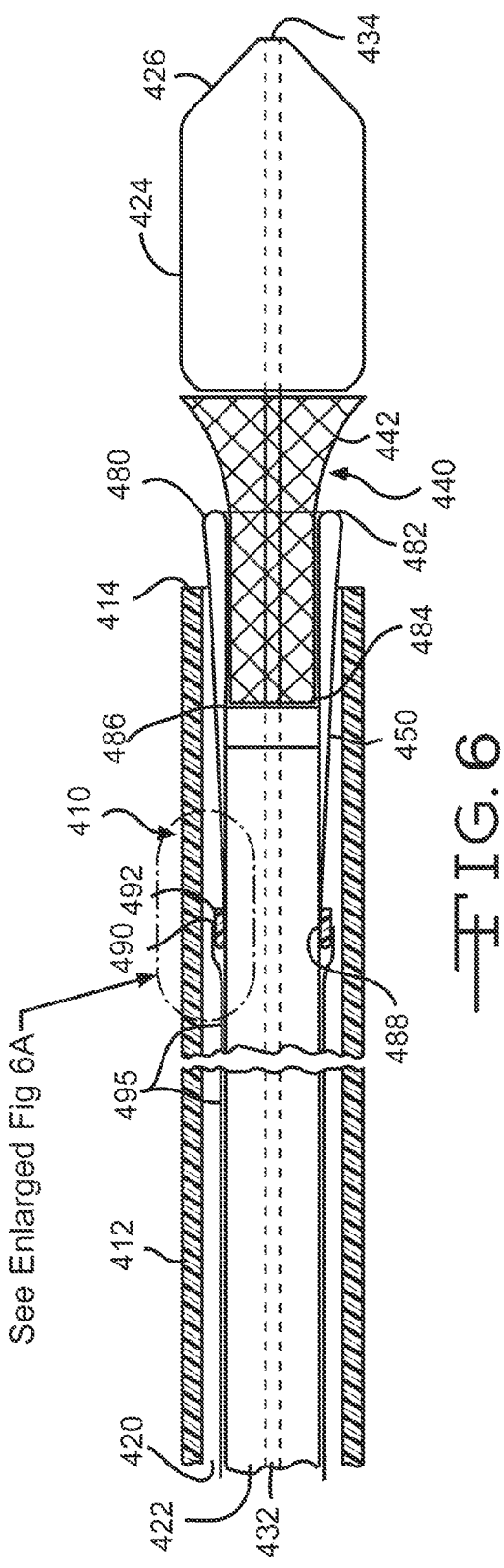

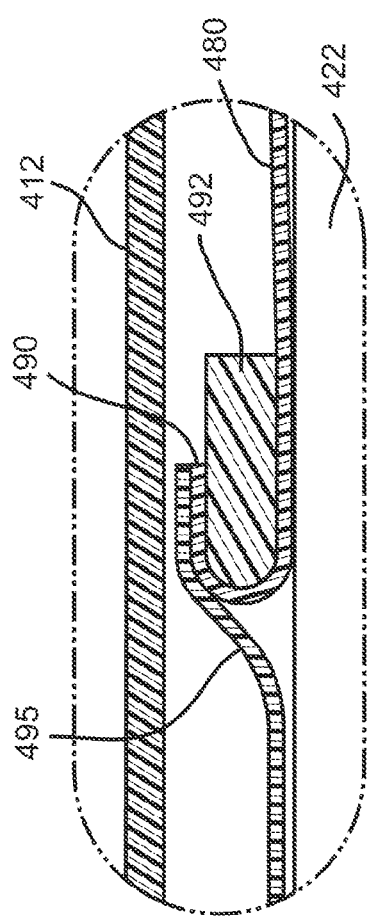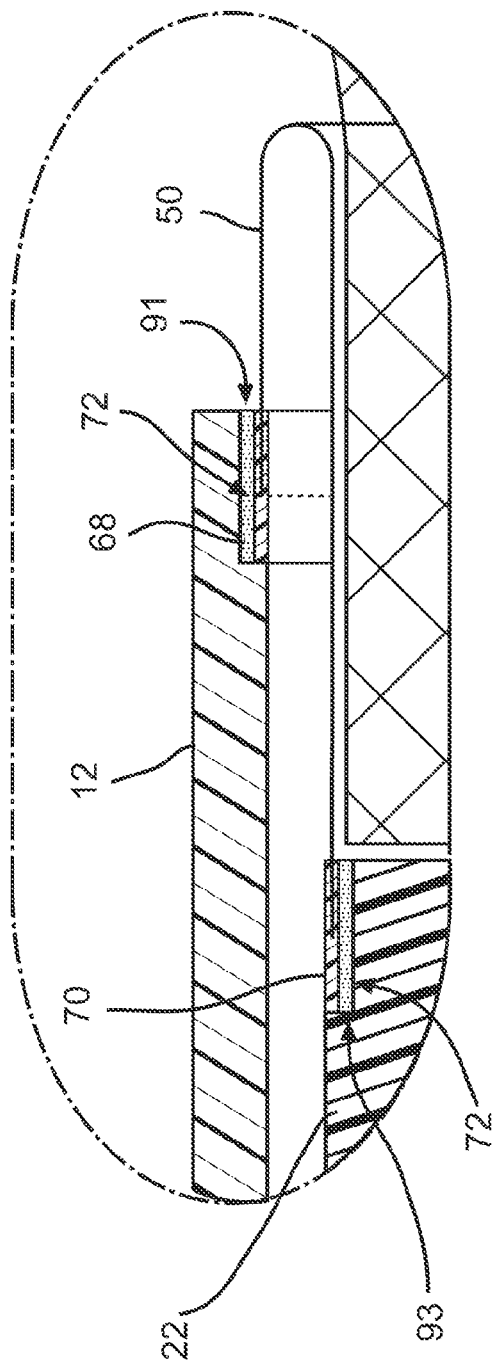

DELIVERY SYSTEM WITH MEDICAL DEVICE RELEASE BY EVERTABLE SLEEVE

CROSS REFERENCE TO RELATED APPLICATIONS

This application is a continuation of co-pending U.S. Nonprovisional application Ser. No. 12/833,604, filed on Jul. 9, 2010 and which claims the benefit of U.S. Provisional Application Ser. No. 61/224,360, filed on Jul. 9, 2009. The entire contents of each of these related applications are incorporated into this disclosure by reference.

FIELD

The disclosure relates generally to the field of intraluminal medical devices. More particularly, the disclosure relates to delivery systems for deploying intraluminal medical devices at a point of treatment within a body vessel.

The technologies described herein are useful in the delivery and deployment of various types of intraluminal medical devices, including stents, stent grafts, occluders, valve devices, expandable filters, and others.

BACKGROUND

Minimally invasive techniques and instruments for placement of intraluminal medical devices have been developed over recent years and are frequently used to deliver and deploy an intraluminal medical device at a desired point of treatment. In these techniques, a delivery system is used to carry the intraluminal medical device through a body vessel to the point of treatment. Once the point of treatment is reached, the intraluminal medical device is deployed from the delivery system. The delivery system is subsequently withdrawn from the point of treatment and, ultimately, the body vessel.

A wide variety of intraluminal medical devices that utilize minimally invasive technology has been developed and include stents, stent grafts, occlusion devices, infusion catheters, prosthetic valves, and the like. These devices are frequently used in a variety of treatment procedures. For example, self-expandable stents are used to provide support to various vessels and ducts in the cardiovascular and gastrointestinal systems. Also, prosthetic valves, including prosthetic venous valves, are used to introduce or restore a valving function to a body vessel.

Loading an intraluminal medical device into and deploying the device from a conventional delivery system involves relative movement between the intraluminal medical device and a sheath or other outer tubular member that maintains the device in a compressed state during navigation to the point of treatment. During a loading operation, the intraluminal medical device typically is concentrically oriented with an inner dilator. The dilator and intraluminal medical device are then slidingly inserted into a surrounding sheath. During deployment, relative movement between the dilator and sheath is used until the intraluminal medical device is fully exposed. Typically, the dilator and intraluminal medical device are caused to slide out of the sheath, either by retraction of the sheath, advancement of the dilator, or a combination of both. Eventually, the sheath is no longer able to maintain the device in its compressed state due to the change in relative position(s), and the intraluminal medical device is deployed from the dilator to take its implanted position at the point of treatment within the body vessel.

The friction that occurs between the intraluminal medical device and the inner surface of the surrounding sheath presents an opportunity for damage to occur to the intraluminal medical device. This is particularly true for intraluminal medical devices that include a graft or other material attached to a support frame, such as stent grafts, valve devices with attached leaflets or other valve functional member, tissue graft devices, graft-based occluders, and other devices. If an excessive amount of friction occurs, the attachment between the graft or other material and the support frame can be damaged, which might affect performance of the device. Use of a tacky valve or valve component can also present additional challenges during loading and/or deployment. Damage to the graft or other material itself might also occur.

Friction within delivery systems poses a risk for intraluminal medical devices that require an input of force to achieve intraluminal expansion, such as balloon expandable stents and similar devices, but the problem is of particular concern for self-expandable intraluminal medical devices due to the primary functional role played by the sheath in maintaining these devices in their compressed configurations prior to deployment. With a sheath that provides the constraining force that prevents expansion, friction during relative movement of the dilator or other carrier device and the sheath is a necessary result.

Accordingly, a need exists for a delivery system with an improved release mechanism for expandable intraluminal medical devices.

BRIEF SUMMARY OF DESCRIBED EMBODIMENTS

Medical device delivery systems are described.

A delivery system according to a first embodiment comprises a tubular member having a proximal end defining a proximal opening, a distal end defining a distal opening, and an inner surface defining a passageway extending between the proximal and distal openings; an inner member slideably disposed within the passageway of the tubular member, the inner member comprising an elongate body defining an inner passageway adapted to slideably receive a wireguide, a chamber for receiving an expandable intraluminal medical device, and a distal tip adapted for navigation through a body vessel, the chamber having a second proximal end and a second distal end; an expandable intraluminal medical device disposed on the inner member at the chamber; and an evertable sleeve attached to the inner member proximal to the chamber and to the inner surface of the tubular member at the distal end.

A delivery system according to a second embodiment comprises a tubular member having a proximal end defining a proximal opening, a distal end defining a distal opening, and an inner surface defining a passageway extending between the proximal and distal openings; an inner member slideably disposed within the passageway of the tubular member, the inner member comprising an elongate body defining an inner passageway adapted to slideably receive a wireguide, a chamber for receiving an expandable intraluminal medical device, and a distal tip adapted for navigation through a body vessel, the chamber having a second proximal end and a second distal end and comprising an axial section of the inner member having a reduced diameter as compared to a proximal portion of the inner member; an expandable intraluminal medical device disposed on the inner member at the chamber; and an evertable sleeve attached to the inner member proximal to the chamber and to the inner surface of the tubular member at the distal end.

A delivery system according to a third embodiment comprises a tubular member having a proximal end defining a proximal opening, a distal end defining a distal opening, and an inner surface defining a passageway extending between the proximal and distal openings; an inner member slideably disposed within the passageway of the tubular member, the inner member comprising an elongate body defining an inner passageway adapted to slideably receive a wireguide, a chamber for receiving an expandable intraluminal medical device, and a distal tip adapted for navigation through a body vessel, the chamber having a second proximal end and a second distal end and comprising an axial section of the inner member having a reduced diameter as compared to a proximal portion of the inner member; an expandable intraluminal medical device disposed on the inner member at the chamber; and an evertable sleeve attached to the inner member proximal to the chamber and to the inner surface of the tubular member at the distal end; the evertable sleeve comprising a flexible tubular member having a second proximal end and a second distal end embedded within a flange having a rounded inner edge; the second proximal end extends proximally along a portion of the inner member proximal to the chamber; and the second distal end extends distally along a portion of the inner surface of the tubular member toward the distal end.

Additional understanding of these and other embodiments can be obtained with review of the detailed description, below, and the appended drawings.

BRIEF DESCRIPTION OF THE DRAWINGS

FIG. 3 is a sectional view of the distal end of a delivery system according to a second embodiment. An associated intraluminal medical device is illustrated in a partially deployed state.

FIG. 4 is a sectional view of the distal end of a delivery system according to a third embodiment. An associated intraluminal medical device is illustrated in a partially deployed state.

FIG. 5 is a partial sectional view of the distal end of a delivery system according to a fourth embodiment. An associated intraluminal medical device is illustrated in a partially deployed state.

FIG. 6 is a partial sectional view of the distal end of a delivery system according to a fifth embodiment. An associated intraluminal medical device is illustrated in a partially deployed state.

FIG. 6A is a magnified view of the area indicated in FIG. 6.

FIG. 7 is a magnified sectional view of the distal end of a delivery system according to an alternative embodiment.

DETAILED DESCRIPTION OF EXEMPLARY EMBODIMENTS

The following detailed description and the appended drawings describe and illustrate various exemplary embodiments of the invention. The description and drawings are exemplary in nature and are provided to enable one skilled in the art to make and use one or more embodiments according to the disclosure. They are not intended to limit the scope of the claims in any manner.

As used herein, the term "evertable" refers to the ability to have an inner surface turned outward.

Figure 1:
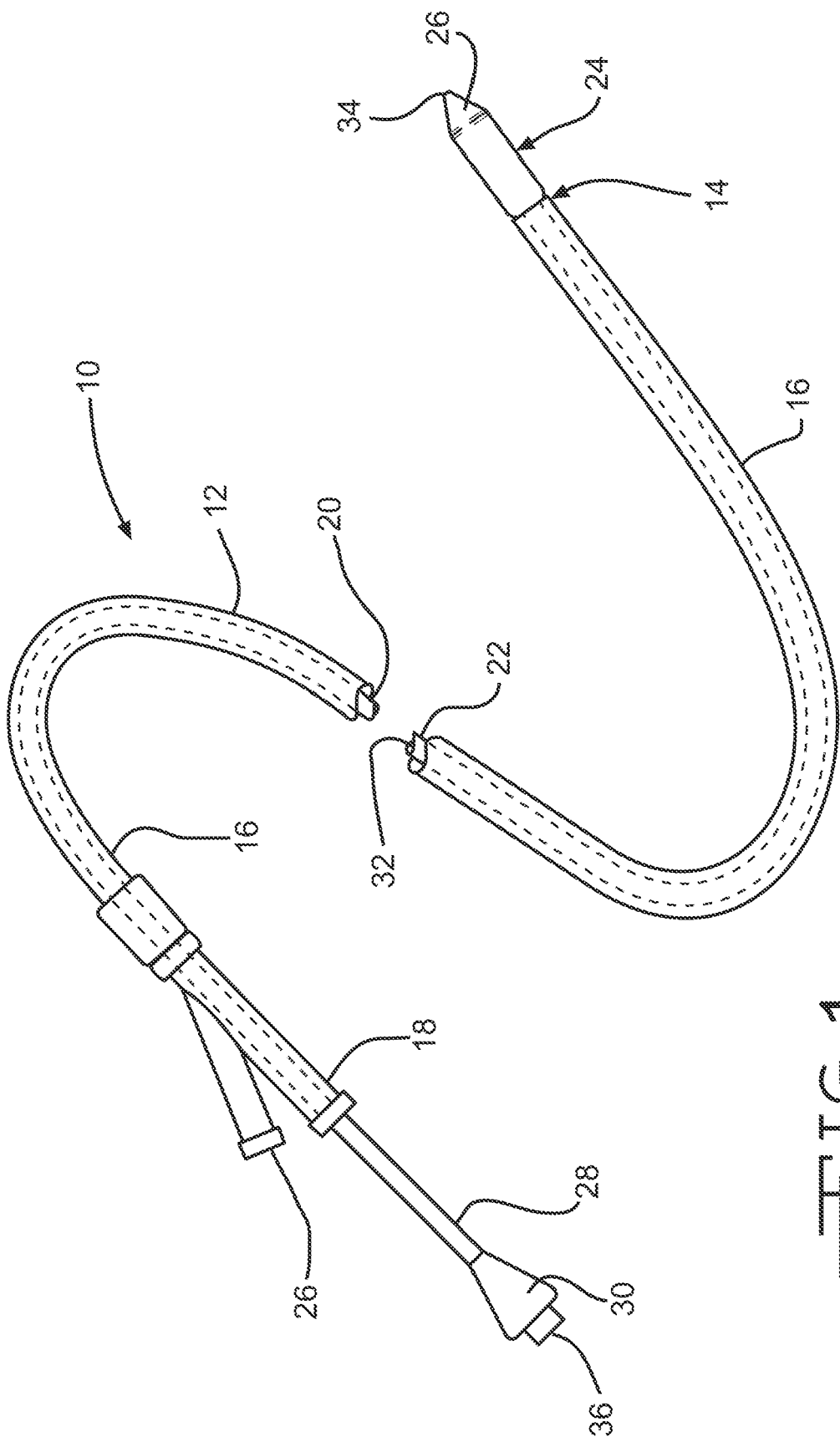
FIG. 1 is a perspective view of a delivery system according to a first embodiment.
Figure 2:
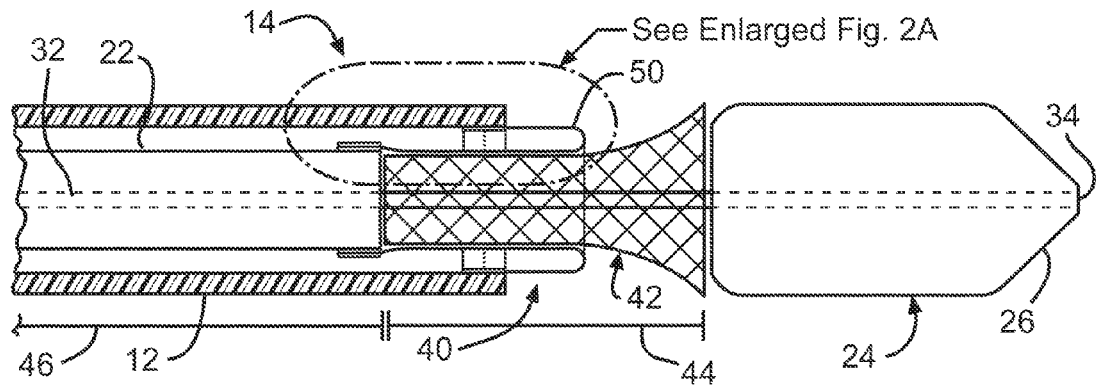
FIG. 2 is a sectional view of the distal end of the delivery system illustrated in FIG. 1. An associated intraluminal medical device is illustrated in a partially deployed state.
Figure 2A:
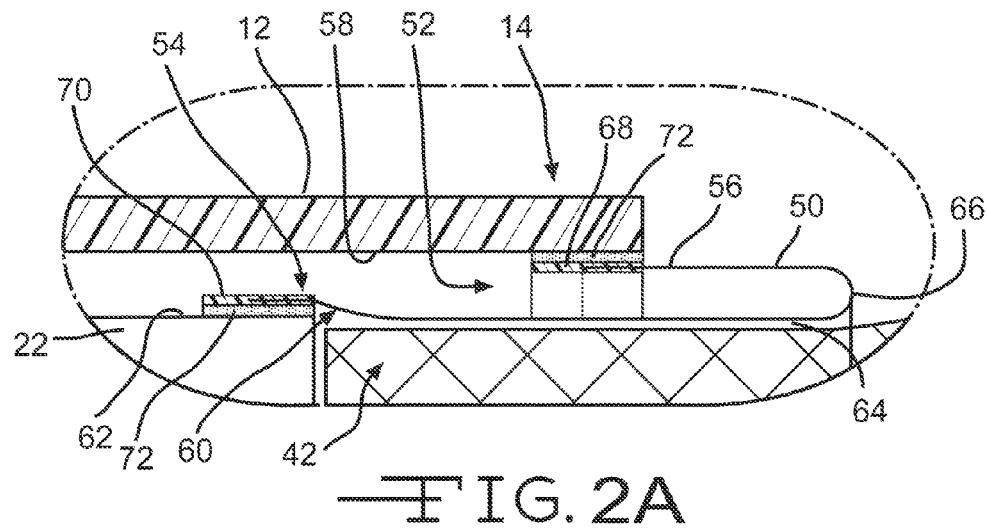
FIG. 2A is a magnified view of the area indicated in FIG. 2.

FIGS. 1, 2, and 2A illustrate a delivery system 10 according to a first embodiment. The delivery system 10 includes an elongate sheath or tubular member 12 having a distal end 14 which is insertable in a body vessel and a proximal end 16 that can be coupled to a connector 18 such as a Touhy Borst adapter or any other suitable functional connectors, adapters, and the like. A passageway or lumen 20 extends from the distal end 14 to the proximal end 16 and permits relative axial movement of components contained therein, such as dilator 22, described below.

Dilator 22 or another suitable inner member is disposed within the passageway 20 defined by the tubular member 12. As used herein, the term "dilator" refers to an elongate member capable of being disposed within a lumen of a sheath, such as the tubular member 12, and adapted to have an intraluminal medical device positioned thereon, as described in detail below. The dilator 22 has a distal tip 24 that defines a tapered distal end 26. The distal end 26 provides an atraumatic structure that facilitates insertion of the delivery system 10 into a body vessel and subsequent navigation of the delivery system 10 through the body vessel. A proximal end 28 of the dilator 22 can include one or more structures that facilitate handling of the dilator 22 and/or delivery system 10, such as tab 30.

A lumen 32 is formed by the dilator 22 and extends along the entire length of the dilator 22, from the distal end 26 to the proximal end 28. Distal 34 and proximal 36 openings defined by the dilator 22 provide access to the lumen 32. The lumen 32 is adapted to receive a wireguide (not shown) or any other suitable member, therein. As used herein, the term "wireguide" refers to elongate members used in minimally invasive procedures to define a path along which other devices can be advanced. The term is considered equivalent in meaning to the term "guidewire" as used in the art. The lumen 32 aids in guiding the delivery system 10 through a body vessel to a desired point of treatment by ensuring that axial advancement of the delivery system 10 occurs only along the path defined by a previously placed wireguide.

While the embodiment illustrated in FIGS. 1, 2 and 2A includes a lumen 26 that extends along the entire length of the dilator, it is understood that an alternative lumen can be used. For example, a lumen that extends along only a portion of the length of the dilator 22 can be used. Indeed, over-the-wire, rapid exchange, short wire and intraductal exchange type delivery systems are contemplated and considered to be within the scope of the invention.

In use, the delivery system 10 is placed over a wireguide that has been placed in a body vessel such that a distal end of the wireguide is near or beyond a desired point of treatment relative to a point at which the wireguide enters the vessel. The delivery system 10 is placed over the wireguide by passing the proximal end of the wireguide into the distal opening 34 of the dilator 22 and into the lumen 32. The delivery system 10 is then advanced along the wireguide and through the vessel until a desired positioning of a portion of the delivery system 10, such as an portion containing a carried intraluminal medical device, relative to a point of treatment is achieved.

The tubular member 12 and dilator 22 are made of suitable materials currently known in the art or hereinafter developed. The selection of materials for these elements need only address the desired flexibility and biocompatibility recognized as design concerns for medical device delivery systems.

A skilled artisan will be able to select suitable materials for these elements based on various considerations, including the environment in which a particular delivery system according to an embodiment is intended to be used and other considerations. Examples of suitable materials include polymeric materials, such as polypropylene and nylon, extruded or otherwise formed into the desired structures.

As best illustrated in FIG. 2, the dilator 22 defines a device chamber 40 for receiving an expandable intraluminal medical device 42. In the illustrated embodiment, the chamber 40 is positioned proximal to the distal tip 24 and comprises an axial section 44 along the length of the dilator 22 having a reduced diameter as compared to the proximal portion 46 of the dilator 22. While this structure of the chamber 40 is considered advantageous for use with some expandable intraluminal medical devices, such as those including an attached graft member or other component that increases the overall bulk of the expandable intraluminal medical device, alternative structures can be used. For example, the chamber 40 can comprise a simple mounting region having the same diameter as the remainder of the dilator 22 proximal to the distal tip 24. In these embodiments, which are considered advantageous for use with expandable support frames, stents, and other devices without attached graft members, the expandable intraluminal medical device is simply positioned on the mounting region of the dilator 22.

While the expandable intraluminal medical device 42 is illustrated as an expandable stent, it is expressly understood that any suitable expandable intraluminal medical device can be used in delivery systems according to the invention. Further, the intraluminal medical device 42 can be a self-expandable device or a device that requires an input of force for expansion, such as a balloon-expandable device. Examples of expandable intraluminal medical devices that can be used in the delivery systems disclosed herein include stents, stent grafts, valve devices, occluders, expandable filters, distal protection devices, and the like. The delivery systems described herein are believed to be particularly well-suited for use with expandable intraluminal medical devices that include a graft member attached to a support frame. As used herein, the term "graft member" refers to natural and synthetic sections of material, such as polymeric materials, natural tissue, and other flexible sections of material. Examples of such devices include stent grafts and prosthetic valves. Specific examples of suitable self-expandable medial devices for use with delivery systems according to the invention include those described in U.S. Pat. No. 6,200,336 to Pavcnik et al. for a MULTIPLE-SIDED INTRALUMINAL MEDICAL DEVICE; U.S. patent application Ser. No. 10/642,372 of Pavcnik et al. for an IMPLANTABLE VASCULAR DEVICE, filed on Aug. 15, 2003; and U.S. patent application Ser. No. 10/828,716 of Case et al. for an ARTIFICIAL VALVE PROSTHESIS WITH IMPROVED FLOW DYNAMICS, filed on Apr. 21, 2004; the entire disclosures of which are hereby incorporated into this disclosure for the purpose of describing suitable self-expandable medical devices for use with delivery systems according to the invention.

As best illustrated in FIG. 2A, an evertable sleeve 50 is positioned between the tubular member 12 and the dilator 22. The evertable sleeve 50 is a flexible tubular member having distal 52 and proximal 54 ends and a sleeve body extending between the proximal and distal ends. An outer surface 56 of the distal end 52 is attached to an inner surface 58 of the distal end 14 of the tubular member 12, while an inner surface 60 of the proximal end 54 is attached to an outer surface 62 of the dilator 22 at a point proximal to the device chamber 40 or other portion of the dilator 22 with which the expandable intraluminal medical device 42 is associated. The details of the attachment illustrated in the figures are described in further detail below. This structural arrangement allows an inner surface 64 of the evertable sleeve 50 to be positioned adjacent the expandable intraluminal medical device 42 while in the device chamber 40 or other suitable region of the dilator 22. As will be described below, this positioning of the inner surface 64 shields the expandable intraluminal medical device from contact with the tubular member 12 and the friction that would be created between the tubular member 12 and the expandable intraluminal medical device in the absence of the evertable sleeve. Furthermore, the structural arrangement between the evertable sleeve 50, the tubular member 12 and the dilator 22 allows the formation of rolling bend 66 in the evertable sleeve 50.

In the embodiment illustrated in FIG. 2A, the outer surface 56 at the distal end 52 of the evertable sleeve 50 and the inner surface 60 at the proximal end 54 of the evertable sleeve 50 are portions of the same continuous surface of the sleeve 50.

The attachment between the distal end 52 of the evertable sleeve 50 and the inner surface 58 of the distal end 14 of the tubular member 12 avoids various disadvantages that might result from attaching the distal end 52 to an exterior surface of the tubular member 12. For example, an attachment to the exterior surface of the tubular member 12 would increase the overall exterior diameter of the delivery system 10 at the point of attachment, which might affect the use of the delivery system 10 in certain body vessels. Furthermore, such an attachment would likely produce an irregularity on the exterior surface of the tubular member 12 that might cause irritation or other damage to a body vessel as a result of navigation of the delivery system 10 therethrough.

Figure 2B:
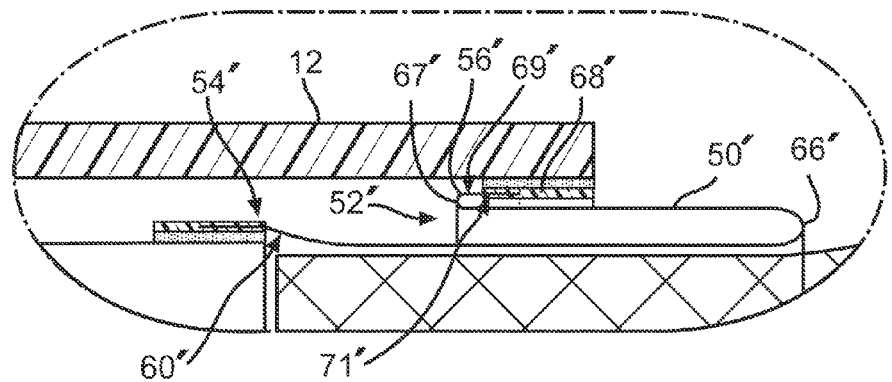
FIG. 2B is a magnified sectional view of the distal end of a delivery system according to an alternative embodiment.

FIG. 2B illustrates an alternative structure for the attachment between the evertable sleeve and the tubular member. In contrast to the embodiment illustrated in FIG. 2A, the outer surface 56' at the distal end 52' of the evertable sleeve 50' and the inner surface 60' at the proximal end 54' of the evertable sleeve 50' are portions of opposing surfaces of the sleeve 50'. This alternative embodiment is discussed in detail below.

As best illustrated in FIG. 2A, the distal end 52 of the sleeve 50 is embedded in a distal flange 68 and the proximal end 54 is embedded in a proximal flange 70. While the inclusion of the flanges 68, 70 is considered optional, their inclusion is considered advantageous at least because the embedding of the ends 52, 54 of the evertable sleeve 50 therein is expected to increase the overall durability of the attachments between the sleeve 50 and the tubular member 12 and the dilator 22 by avoiding direct attachment between these elements. One or both flanges 68, 70 can be included. If included, the flanges 68, 70 advantageously comprise ring structures formed of polymeric material within which a portion of the evertable sleeve 50, such as an end, can be embedded, such as during manufacturing of the delivery system 10. A continuous ring structure is considered advantageous for the flanges 68, 70 at least because it maximizes the surface area for contact between the flanges 68, 70 and the tubular member and/or dilator 22. Intermittent or partial ring structures can be used, though, and may be desirable in particular embodiments.

The flanges 68, 70 are attached to the tubular member 12 and dilator 22, as appropriate, with adhesive 72 or other suitable means for attaching the material of the flanges 68, 70 to the material of the tubular member 12 and the dilator 22. Use of an adhesive is considered advantageous at least because of the availability of a wide range of biocompatible adhesives. Other suitable means for attaching the flanges 68, 70 to the tubular member 12 and dilator 22 include mechanical attachment elements, such as sutures, weld joints, fusion joints, such as joints formed by melting and joining the components together, and other suitable elements and processes for attaching the materials of these elements together. Furthermore, while the figures illustrate both flanges 68, 70 as being attached to the appropriate one of the tubular member 12 and the dilator 22, it is expressly understood that different means for attaching could be used for the flanges 68, 70. For example, the distal flange 68 could be attached to the tubular member 12 with an adhesive while the proximal flange 70 could be attached to the dilator 12 with a mechanical means for attaching, such as a circumferential retainer clip.

FIG. 7 illustrates an alternate embodiment in which the tubular member 12 defines a first recess 91 and the dilator 22 defines a second recess 93. The distal flange 68 is positioned within the first recess 91 and attached to the tubular member with adhesive 72. Similarly, the proximal flange 70 is positioned within the second recess 93 and attached to the dilator 22 with adhesive 72. While the structures illustrated in the other figures is regarded to be within the scope of the invention, the structure illustrated in FIG. 7 is considered advantageous at least because it substantially removes the adhesive 72 and flanges 70 from the interior space between the tubular member 12 and dilator 22. This arrangement is expected to facilitate movement of the evertable sleeve 50 as described herein. It is expressly understood that this optional structural arrangement of the elements can be used with any embodiment described herein.

FIG. 2B illustrates an alternative embodiment in which the distal end 52' of the evertable sleeve 50' is embedded in a proximal end 69' of the distal flange 68'. Also, the proximal end 69' of the distal flange 68' includes a rounded inner edge 71'. This arrangement lessens the tension placed on the evertable sleeve 50' during retraction of the tubular member 12 by forcing the distal end 52' of the evertable sleeve to wrap around the distal flange 68' during such retraction. Furthermore, the presence of the rounded inner edge 71' eliminates an angled surface that might otherwise cause damage to the sleeve 50' when in contact with the distal flange 68'. As a result of this structural arrangement, the evertable sleeve 50 forms first 66' and second 67' rolling bends.

The evertable sleeve 50 can be formed of any suitable material, and a skilled artisan will be able to select an appropriate material based on various considerations, such as the nature of the expandable intraluminal medical device, the environment in which the device is intended to be implanted, and others. The evertable sleeve is advantageously formed of a material that is able to slide against itself and that is sufficiently flexible to form one or more rolling bends during operation of the delivery system, as described above. Examples of materials that are currently considered suitable include ePTFE, nylon, polyethylene, and other polymeric materials. Polyethylene materials are considered particularly advantageous at least because of their bi-axial long-chain structures, which provides beneficial strength characteristics. Materials coated with a lubricious coating are also considered suitable. The sleeve 50 can also have any suitable configuration, including a tubular configuration with uniform inner and/or outer diameters. A tapered sleeve, i.e., a sleeve with an inner and/or outer diameter that varies along an axial length of the sleeve, is believed to be advantageous in that the tapered structure is expected to facilitate movement of the sleeve as described herein. Embodiments in which the sleeve comprises a tapered sleeve, with a first end have a relatively large inner and/or outer diameters is attached to a tubular member as described herein and a second end having a relatively small inner and/or outer diameters is attached to the dilator are believed to be particularly advantageous in that movement of the sleeve as described herein is expected to be facilitated by this arrangement.

The flanges can comprise portions of the evertable sleeve 50 or can be separately attached members, as illustrated in the figures. For example, the flanges can comprise thickened portions of the sleeve 50, treated portions of the sleeve 50, or a polymeric or other structure into which portions, such as an end 52, 54, have been placed. Also, other structures can be used as alternatives to the tubular evertable sleeve 50. For example, two or more strips of material can be attached to the components of and positioned within the delivery system as described herein. A sleeve with lengthwise, partial circumferential, and diagonal (all with respect to a lengthwise axis of the sleeve) slits or other structural disruptions in the surface can also be used.

FIG. 3 illustrates a delivery system 110 according to another exemplary embodiment. The delivery system 110 according to this embodiment is similar to the delivery system 10 illustrated in FIGS. 1, 2 and 2A and described above, except as detailed below. Thus, the delivery system 110 includes an elongate sheath or tubular member 112 having distal 114 and proximal (not illustrated in FIG. 3) ends and a passageway or lumen 120 that extends between the ends. A dilator 122 is disposed within the passageway 120 and has a distal tip 124 that defines a tapered distal end 126. A lumen 132 extends along the entire length of the dilator 122 and distal 134 and proximal (not illustrated in FIG. 3) openings provide access to the lumen 132. A device chamber 140 receives an expandable intraluminal medical device 142. An evertable sleeve 150 is positioned between the tubular member 112 and the dilator 122.

In this embodiment, the distal end 152 of the evertable sleeve 150 is attached to the inner surface 158 of the distal end 114 of the tubular member 112 by retaining ring 180. The retaining ring 180 is a circumferential member that is friction fit into a circumferential groove 182 defined by the inner surface 158 of the tubular member 112. In the embodiment illustrated in FIG. 3, the distal end 152 of the evertable sleeve 150 is embedded into the distal side 184 of the retaining ring 180. As illustrated in the Figure, the distal end 152 is positioned such that the distal end 152 of the sleeve 150 extends distally with respect to the tubular member 112 and lies substantially parallel to the inner surface of the inner surface 158 of the tubular member 112.

In an alternative embodiment, the distal end 152 of the evertable sleeve 150 is embedded into the proximal side 186 of the retaining ring 180—substantially the opposite of the configuration illustrated in FIG. 3. In this embodiment, the distal end 152 of the evertable sleeve 150 extends proximally with respect to the tubular member 112 and wraps around the inner surface 188 of the retaining ring 180. Similar to the embodiment illustrated in FIG. 2B, this structural arrangement is considered advantageous at least because, as compared to the embodiment illustrated in FIGS. 1, 2, and 2A, it is believed to lessen the tension placed on the evertable sleeve 150 during retraction of the tubular member 112. Also, as illustrated in FIG. 3, the inner surface 188 can advantageously define an outer curve to minimize the potential effect of angles on the evertable sleeve 150 while in contact with the surface 188. Furthermore, this alternate structural arrangement achieves this desirable effect on the tension placed on the evertable sleeve 150 while avoiding the introduction of multiple rolling bends, as with the embodiment illustrated in FIG. 2B. While the existence of multiple rolling bends is not considered particularly disadvantageous, the presence of multiple bends is expected to affect the overall bulk and complexity of the delivery system components. As such, for delivery systems for which these factors are a concern, construction according to the structural arrangement according to this embodiment may provide advantages.

FIG. 4 illustrates a delivery system 210 according to another exemplary embodiment. The delivery system 210 according to this embodiment is similar to the delivery system 10 illustrated in FIGS. 1, 2 and 2A and described above, except as detailed below. Thus, the delivery system 210 includes an elongate sheath or tubular member 212 having distal 214 and proximal (not illustrated in FIG. 4) ends and a passageway or lumen 220 that extends between the ends. A dilator 222 is disposed within the passageway 220 and has a distal tip 224 that defines a tapered distal end 226. A lumen 232 extends along the entire length of the dilator 222 and distal 234 and proximal (not illustrated in FIG. 4) openings provide access to the lumen 232. A device chamber 240 receives an expandable intraluminal medical device 242. An evertable sleeve 250 is positioned between the tubular member 212 and the dilator 222.

In this embodiment the distal end 252 of the evertable sleeve 250 is attached to pull wires 290, 292. The pull wires 290, 292 extend proximally through the passageway 220 defined by the tubular member 212 and extends out of the proximal end (not illustrated) of the tubular member 212. This structural arrangement allows a user to retract the evertable sleeve 250 by retracting the pull wires 290, 292 relative to the dilator 222. As illustrated in FIG. 4, the distal end 252 of the evertable sleeve 250 advantageously includes a distal flange 268 as described above. The inclusion of the flange is believed to increase the ruggedness of the connection between the pull wires 290, 292 and the flange 268, which can be formed in any suitable manner, including with adhesives and other bonding agents and/or techniques, by passing the wires 290, 292 through the thickness of the flange 268 and crimping, tying or otherwise fastening the wires 290, 292 to themselves, or with other suitable structures or techniques for attaching wire members to sheet-like material. The pull wires 290, 292 can be formed of any suitable material including metallic wire, string, etc. No limitation on material is contemplated by use of the term "wire". Furthermore, while two pull wires spaced equidistantly from a lengthwise axis of the sleeve and on the same plane are illustrated in the Figure, any suitable number and configuration of wire(s) can be used.

The use of pull wires 290, 292 to control the evertable sleeve 250 may be advantageous in which it is desirable to control the position of the sleeve 250 relative to the expandable intraluminal medical device independent of the position of the tubular member 212.

FIG. 5 illustrates a delivery system 310 according to another exemplary embodiment. The delivery system 310 according to this embodiment is similar to the delivery system 10 illustrated in FIGS. 1, 2 and 2A and described above, except as detailed below. Thus, the delivery system 310 includes an elongate sheath or tubular member 312 having distal 314 and proximal (not illustrated in FIG. 5) ends and a passageway or lumen 320 that extends between the ends. A dilator 322 is disposed within the passageway 320 and has a distal tip 324 that defines a tapered distal end 326. A lumen 332 extends along the entire length of the dilator 322 and distal 334 and proximal (not illustrated in FIG. 5) openings provide access to the lumen 332. A device chamber 340 receives an expandable intraluminal medical device 342. An evertable sleeve 350 is positioned between the tubular member 312 and the dilator 322.

In this embodiment the distal end 352 of the evertable sleeve 350 is attached to an internal tubular member 395 that is disposed within the passageway 320 defined by the sheath or outer tubular member 312 and extends out of the proximal end (not illustrated) of the tubular member 312. This structural arrangement allows a user to retract the evertable sleeve 350 by retracting the inner tubular member 395 relative to the dilator 322. The distal end 352 of the evertable sleeve 350 is attached to the outer surface of the internal tubular member 395, such as by adhesives, thermal bonding, or other suitable attachments. Alternatively, the internal tubular member 395 can be an extension of the evertable sleeve 350, and indeed the internal tubular member 395 and evertable sleeve 350 can comprise a continuous unitary sleeve. Similarly, the proximal end 354 of the evertable sleeve 350 is attached to an outer surface of the dilator 322.

The inclusion of the internal tubular member 395 to control the evertable sleeve 350 is considered advantageous at least because it provides the ability to control the position of the sleeve 350 relative to the expandable intraluminal medical device 342 independent of the position of the tubular member 212, as described above in connection with the embodiment illustrated in FIG. 4, without the inclusion of wire members. A tubular structure may provide additional control over that provided by one or more wire members, as described above, at least because it requires manipulation of only a single element to affect positioning of the sleeve 350 relative to the expandable intraluminal medical device, as opposed to requiring manipulation of two or more members.

FIGS. 6 and 6A illustrate a delivery system 410 according to another exemplary embodiment. The delivery system 410 according to this embodiment is similar to the delivery system 310 illustrated in FIG. 5 and described above, except as detailed below. Thus, the delivery system 410 includes an elongate sheath or tubular member 412 having distal 414 and proximal (not illustrated in FIG. 6) ends and a passageway or lumen 420 that extends between the ends. A dilator 422 is disposed within the passageway 420 and has a distal tip 424 that defines a tapered distal end 426. A lumen 432 extends along the entire length of the dilator 422 and distal 434 and proximal (not illustrated in FIG. 6) openings provide access to the lumen 432. A device chamber 440 receives an expandable intraluminal medical device 442. An evertable sleeve 450 is positioned between the tubular member 412 and the dilator 422.

In this embodiment the evertable sleeve 450 comprises separate individual flaps 480, 482. Proximal ends 484, 486 of the flaps 480, 482 are attached to an outer surface of the dilator 422. Distal ends 488, 490 the flaps 480, 482 are attached to an internal tubular member 495 that is disposed within the passageway 420 defined by the sheath or outer tubular member 412 and extends out of the proximal end (not illustrated) of the tubular member 412. As best illustrated in FIG. 6A, the distal ends 488, 490 of the flaps 480, 482, and the distal end of the internal tubular member 495 can be attached, either directly or via an attachment to each other, to a separate flange member, such as circumferential flange 492.

While two separate flaps are illustrated in the figure, any suitable number, configuration and arrangement of flaps can be used and a skilled artisan will be able to determine acceptable numbers, configurations, and arrangements for particular embodiments based on various considerations, including the nature of the expandable intraluminal medical device with which the delivery system is used or intended to be used.

The foregoing detailed description provides exemplary embodiments of the invention and includes the best mode for practicing the invention. The description and illustration of embodiments is intended only to provide examples and not to limit the scope of the claims in any manner.

What is claimed is:

1. A medical device delivery system, comprising:
a tubular member having a tubular member proximal end defining a tubular member proximal opening, a tubular member distal end defining a tubular member distal opening, and a tubular member inner surface defining a passageway extending between the tubular member proximal and tubular member distal openings;
an inner member slideably disposed within the passageway of the tubular member, the inner member comprising an elongate body defining an inner passageway adapted to slideably receive a wireguide, a chamber for receiving an expandable intraluminal medical device, and a distal tip adapted for navigation through a body vessel, the chamber having a chamber proximal end and chamber distal end;
an expandable intraluminal medical device disposed on the inner member at the chamber; and
an evertable sleeve having an evertable sleeve proximal end attached to the inner member proximal to the chamber and having an evertable sleeve distal end attached to the tubular member inner surface at the tubular member distal end, and having an evertable sleeve body extending between the evertable sleeve proximal end and the evertable sleeve distal end the evertable sleeve comprising a flexible tubular member adapted to move between a first position substantially overlying the expandable intraluminal medical device between the chamber and the tubular member inner surface and a second position substantially proximal to the chamber upon relative axial movement among the tubular member and the inner member;
wherein the evertable sleeve proximal end is attached to the inner member such that, in said first position, the evertable sleeve body extends distally from said evertable sleeve proximal end along a portion of the inner member proximal to the chamber; and
wherein the evertable sleeve distal end is attached to the tubular member inner surface such that, in said first position, the evertable sleeve body extends proximally from said evertable sleeve distal end along a portion of the inner surface of the tubular member toward the tubular member proximal end.

2. The medical device delivery system according to claim 1, wherein the evertable sleeve has an evertable sleeve inner surface and an evertable sleeve outer surface;
wherein the evertable sleeve proximal end of the evertable sleeve inner surface is attached to the inner member; and
wherein the evertable sleeve distal end of the evertable sleeve outer surface is attached to the tubular member inner surface.

3. The medical device delivery system according to claim 1, wherein at least one of the evertable sleeve proximal end and the evertable sleeve distal end comprises a flange.

4. The medical device delivery system according to claim 3, wherein the flange comprises a circumferential ring structure.

5. The medical device delivery system according to claim 3, wherein the flange comprises a partial circumferential ring structure.

6. The medical device delivery system according to claim 1, wherein at least one of the evertable sleeve proximal end and the evertable sleeve distal end is embedded within a flange.

7. The medical device delivery system according to claim 1, wherein the evertable sleeve distal end is embedded within a flange; and
wherein the flange includes a rounded inner edge.

8. The medical device delivery system according to claim 1, wherein the evertable sleeve comprises ePTFE, nylon, or another polymeric material.

9. The medical device delivery system according to claim 1, wherein the expandable intraluminal medical device comprises a self-expandable intraluminal medical device.

10. The medical device delivery system according to claim 1, wherein the expandable intraluminal medical device requires an application of an expansion force to effect expansion.

11. The medical device delivery system according to claim 1, wherein the expandable intraluminal medical device comprises a stent.

12. The medical device delivery system according to claim 1, wherein the expandable intraluminal medical device comprises a valve device.

13. The medical device delivery system according to claim 1, wherein the expandable intraluminal medical device comprises a stent graft, an occluder, an expandable filter, or a distal protection device.

14. The medical device delivery system according to claim 1, wherein the expandable intraluminal medical device includes a graft member.

15. The medical device delivery system according to claim 14, wherein the graft member comprises a natural material.

16. The medical device delivery system according to claim 15, wherein the natural material comprises natural tissue.

17. The medical device delivery system according to claim 14, wherein the graft member comprises a synthetic material.

18. The medical device delivery system according to claim 17, wherein the synthetic material comprises a polymeric material.

19. A medical device delivery system, comprising:
a tubular member having a tubular member proximal end defining a tubular member proximal opening, a tubular member distal end defining a tubular member distal opening, and a tubular member inner surface defining a passageway extending between the tubular member proximal and tubular member distal openings;
an inner member slideably disposed within the passageway of the tubular member, the inner member comprising an elongate body defining an inner passageway adapted to slideably receive a wireguide, a chamber for receiving an expandable intraluminal medical device, and a distal tip adapted for navigation through a body vessel, the chamber having a chamber proximal end and chamber distal end;
an expandable intraluminal medical device disposed on the inner member at the chamber; and
an evertable sleeve attached to the inner member proximal to the chamber and to the tubular member inner surface at the tubular member distal end, the evertable sleeve comprising a flexible tubular member adapted to move between a first position substantially overlying the expandable intraluminal medical device between the chamber and the tubular member inner surface and a second position substantially proximal to the chamber upon relative axial movement among the tubular member and the inner member;
wherein the evertable sleeve has a proximal sleeve end and a distal sleeve end and an evertable sleeve inner surface extending continuously from said proximal sleeve end to said distal sleeve end, and, an evertable sleeve outer surface extending continuously from said proximal sleeve end to said distal sleeve end, the evertable sleeve proximal end of the evertable sleeve inner surface attached to the inner member and the evertable sleeve distal end of the evertable sleeve outer surface attached to the tubular member inner surface.

20. A medical device delivery system, comprising:

a tubular member having a tubular member proximal end defining a tubular member proximal opening, a tubular member distal end defining a tubular member distal opening, and a tubular member inner surface defining a passageway extending between the tubular member proximal and tubular member distal openings;

an inner member slideably disposed within the passageway of the tubular member, the inner member comprising an elongate body defining an inner passageway adapted to slideably receive a wireguide, a chamber for receiving an expandable intraluminal medical device, and a distal tip adapted for navigation through a body vessel, the chamber having a chamber proximal end and chamber distal end;

an expandable intraluminal medical device disposed on the inner member at the chamber; and an evertable sleeve attached to the inner member proximal to the chamber and to the inner surface at the tubular member distal end, the evertable sleeve comprising a flexible tubular member adapted to move between a first position substantially overlying the expandable intraluminal medical device between the chamber and the tubular member inner surface and a second position substantially proximal to the chamber upon relative axial movement among the tubular member and the inner member, said evertable sleeve having an evertable sleeve proximal end, an evertable sleeve distal end, and an evertable sleeve body extending between the evertable sleeve proximal end and the evertable sleeve distal end, said evertable sleeve distal end being embedded within a flange having a rounded inner edge;

wherein the evertable sleeve proximal end is attached to the inner member such that, in said first position, the evertable sleeve body extends distally from said evertable sleeve proximal end along a portion of the inner member proximal to the chamber; and wherein the evertable sleeve distal end is attached to the tubular member inner surface such that, in said first position, the evertable sleeve body extends proximally from said evertable sleeve distal end along a portion of the inner surface of the tubular member toward the tubular member proximal end.

* * * * *